United States Patent
Carroll

(10) Patent No.: US 7,458,968 B2
(45) Date of Patent: *Dec. 2, 2008

(54) DEVICE FOR NEUROCRYO ANALGESIA AND ANESTHESIA

(76) Inventor: Ronald J. Carroll, 255 Western Promenade, Portland, ME (US) 04102

( * ) Notice: Subject to any disclaimer, the term of this patent is extended or adjusted under 35 U.S.C. 154(b) by 29 days.

This patent is subject to a terminal disclaimer.

(21) Appl. No.: 10/857,402

(22) Filed: May 28, 2004

(65) Prior Publication Data

US 2004/0220648 A1 Nov. 4, 2004

Related U.S. Application Data

(62) Division of application No. 10/071,574, filed on Feb. 5, 2002, now Pat. No. 6,761,715.

(60) Provisional application No. 60/286,636, filed on Apr. 26, 2001.

(51) Int. Cl.
*A61B 18/18* (2006.01)
(52) U.S. Cl. .......................... 606/21; 606/23
(58) Field of Classification Search ............. 606/20–26, 606/1; 607/105
See application file for complete search history.

(56) References Cited

U.S. PATENT DOCUMENTS

| | | | |
|---|---|---|---|
| 5,108,390 A | | 4/1992 | Potocky |
| 5,624,392 A * | | 4/1997 | Saab .......................... 604/43 |
| 6,190,370 B1 * | | 2/2001 | Tsui .......................... 604/508 |
| 6,235,019 B1 * | | 5/2001 | Lehmann et al. .............. 606/22 |
| 6,272,370 B1 * | | 8/2001 | Gillies et al. ................ 600/411 |
| 6,379,331 B2 * | | 4/2002 | Barbut et al. ................ 604/113 |
| 6,551,274 B2 * | | 4/2003 | Heiner ....................... 604/113 |
| 6,761,715 B2 * | | 7/2004 | Carroll ........................ 606/21 |

* cited by examiner

*Primary Examiner*—Michael Peffley
(74) *Attorney, Agent, or Firm*—Pierce Atwood LLP; Kevin M. Farrell; David J. Wilson

(57) ABSTRACT

A catheter system and method for selectively cooling or freezing target neuronal tissue to induce lesions along the neuroaxis and produce cryoanalgesia by impairing nerve conduction of the targeted neuronal tissue. The system includes a catheter that has cryogenic capability for variable cooling or freezing of neuronal tissue. The catheter also includes temperature sensing and electrodiagnostic capabilities. A pressurized fluid source is included for inflating a portion of the catheter body. The system includes electrodiagnostic equipment for stimulating and monitoring sensory evoked potentials in the patient. The method involves placement of the catheter tip in the subarachnoid space of the spinal canal and location of the tip on the neuronal target using imaging and electrodiagnostic techniques.

26 Claims, 5 Drawing Sheets

DEVICE FOR NEUROCRYO ANALGESIA AND ANESTHESIA

CROSS REFERENCES TO RELATED APPLICATIONS

This application is a divisional of U.S. patent application Ser. No. 10/071,574 filed Feb. 5, 2002, now U.S. Pat. No. 6,761,715 which claims the benefit of U.S. Provisional Application Ser. No. 60/286,636, filed, Apr. 26, 2001.

BACKGROUND OF THE INVENTION

This invention relates generally to cryoanalgesia and more particularly to devices and procedures for applying cryoanalgesia to the neuroaxis.

Management of acute and chronic pain has been a concern for as long as medicine has been practiced. Many methods of inducing analgesia and anesthesia have been developed. The use of chemical substances is perhaps the most common approach to pain relief. This approach requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

An alternate approach that avoids these drawbacks is cryoanalgesia, which is a safe and effective approach to providing prolonged pain relief without the complications or undesirable after effects often experienced with chemical-based approaches. As used herein, the term "cryoanalgesia" refers to cooling or freezing of neuronal tissue (nerves, synapses, ganglia, etc.) to produce analgesia or anesthesia. Attempts to use tissue cooling or freezing to control pain have been known since antiquity. Surgery using cold packs and the painless amputation of frozen limbs during wartime are part of military medical history. In the nineteenth century, attempts were made to use tissue cooling to treat a wide range of maladies. Twentieth century studies have shown that the cooling or freezing of neuronal tissue reduces or eliminates pain by interrupting nerve conduction. Cooling neuronal tissue to temperatures in the range of zero to −4 degrees centigrade, and sometimes below, causes analgesia lasting from days to weeks. Neuronal tissues cease functioning when sufficiently cooled, but before becoming frozen. Freezing neuronal tissue (i.e., reducing tissue temperature to −4 to −20 degrees centigrade or below) causes profound long lasting, usually permanent but sometimes reversible, anesthesia of the innervated part. There may well be different outcomes of cooling and freezing, depending on whether the treatment is applied to neuronal axons or neuronal cell bodies (containing the nucleus).

A number of devices for the controlled cooling and/or freezing of small volumes of tissue are available. Rigid cryoprobes exist for percutaneous use or in open invasive surgical procedures. For example, cryoprobes are used for freezing a range of lesions from prostate tissue to metastatic cancers in liver. Neuronal tissue has been frozen with such devices for the relief of pain. Such devices have been in use for more than 20 years.

Cryocatheters or cryogenic catheters are of more recent evolution and have been used by way of the blood vascular route to destroy, by freezing, conducting tissues in the heart for the correction of cardiac arrhythmia. Such cyrocatheters are not designed for cryoanalgesia.

In both these types of systems, coolant gases under pressure are delivered to the tip of the instrument (i.e., the probe or catheter) where expansion of the gas is used to create temperatures as low as −60 degrees centigrade or below which cools or freezes the tissues in the local area around the tip. The size and configuration of the lesion created will depend in large part on a configuration of the tip. The effect obtained will depend upon the rate of cooling, degree of cooling, and the duration of cooling, as well as specifics of the tissue and environment.

While conventional cryoprobes used to treat neuronal tissue can produce excellent results, they generally can be used only for certain percutaneous procedures in which the target neuronal tissue is readily accessible by the rigid probes or for open surgical procedures. These restrictions greatly limit the opportunities for using cryoanalgesia. Accordingly, it would be desirable to have a device and method that would allow a more extensive use of cryoanalgesia.

SUMMARY OF THE INVENTION

The above-mentioned need is met by the present invention, which provides a catheter including a catheter body having a proximate end and a distal end, means for holding the distal end adjacent to a neuroaxis structure target, and means for internally delivering a coolant fluid to the distal end of the catheter body. In one possible embodiment, the catheter body is a tube having first and second chambers formed therein. The means for holding includes an expandable portion formed in the tube and a pressurized fluid source connected to the first chamber for inflating the expandable portion, and the means for internally delivering a coolant fluid includes a delivery tube disposed in the second chamber and a source of coolant fluid connected to the delivery tube. A temperature detector can be disposed on an external surface of the catheter body.

The present invention can also include an electrically conductive tip member formed on an external surface of the catheter body, an external electrode for application to a patient's body, and a monitoring/stimulating device electrically connected to the tip member and to the external electrode. The device is capable of delivering an electrical stimulus to the external electrode and measuring sensory evoked potentials in response to input from the tip member.

In use, the distal end of the catheter is inserted into the subarachnoid space of a patient and positioned adjacent to a neuronal tissue target. A portion of the catheter is inflated to hold the distal end in position on the target neuronal tissue. The external electrode is placed on a dermatome on the patient that corresponds to the neuronal tissue target. The monitoring/stimulating device can then be used to deliver an electrical stimulus to the dermatome (which will be transmitted centrally over sensory afferent nerve fibers) and measure resultant sensory evoked potentials detected at the tip member. Measurement of sensory evoked potentials can be used to verify that the distal end is properly positioned relative to the neuronal tissue target, since coolant fluid is delivered into the catheter so as to effect cooling or freezing of the neuronal tissue target and stop neuronal nerve conduction.

The present invention and its advantages over the prior art will become apparent upon reading the following detailed description and the appended claims with reference to the accompanying drawings.

DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
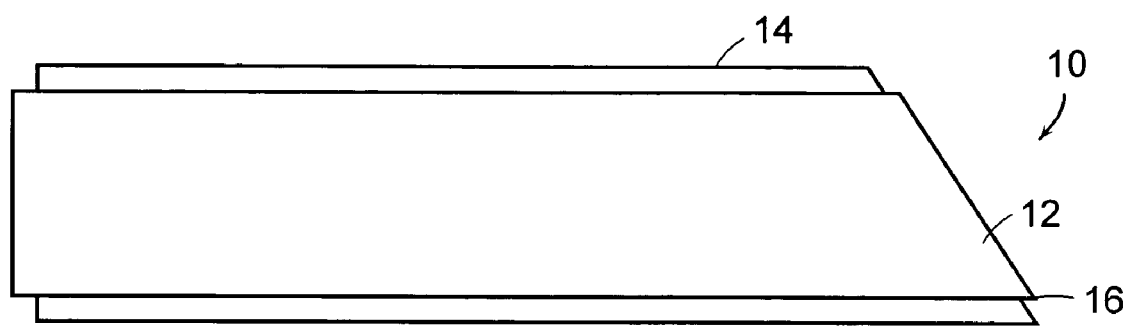
FIG. 1 is a longitudinal cross-sectional view of an introducer from a neuro-cryocatheter system of the present invention.

The highly structured neuroaxis (the spinal cord and spinal nerves) lends itself to cryoanalgesia techniques to produce analgesia or anesthesia of body parts innervated by the target nerve tissue. This is accomplished by selective cooling or freezing of the target neuronal tissue using a neuro-cryocatheter system to induce lesions along the neuroaxis. The neuro-cryocatheter system is used to diagnose, monitor and interfere with nerve conduction along the spinal cord axis by invading the cerebrospinal fluid canal (subarachnoid space) by way of percutaneous puncture. The cooling or freezing of neuronal tissue produces analgesia or anesthesia (i.e., "cryoanalgesia") by impairing nerve conduction of the targeted neuronal tissue. The neuro-cryocatheter system of the present invention may be used not only on human patients but on other animals, particularly vertebrates, as well.

Referring to the drawings wherein identical reference numerals denote the same elements throughout the various views, FIGS. 1-4 show a neuro-cryocatheter system for the cooling or freezing of neuroaxis structure targets. The system includes an introducer 10 shown in FIG. 1. The introducer 10 comprises a stylet 12 encased by a sheath 14. The stylet 12 has a sharp, pointed tip 16 capable of penetrating soft tissue overlying the spinal canal. Once the introducer 10 has been inserted into the desired location, the stylet 12 is removed and the sheath 14 is left in place to function as a cannula. Preferably, the introducer 10 has an outer diameter of about 1.5 millimeters or less and a length of typically 4-5 inches.

Figure 2:
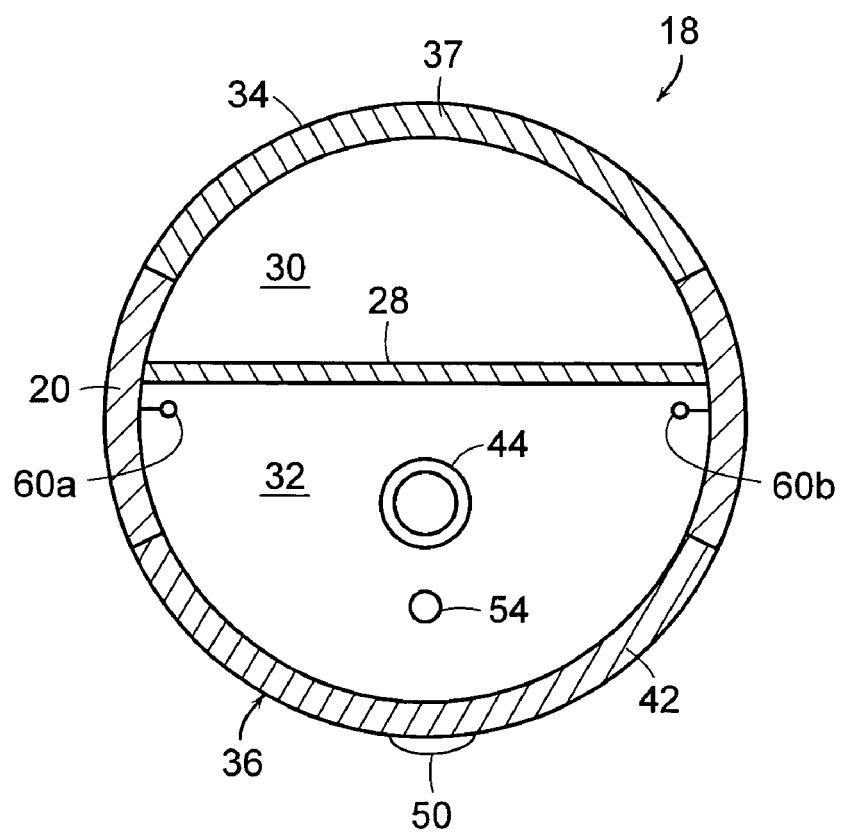
FIG. 2 is a longitudinal cross-sectional view of cryocatheter from a neuro-cryocatheter system of the present invention.
Figure 3:
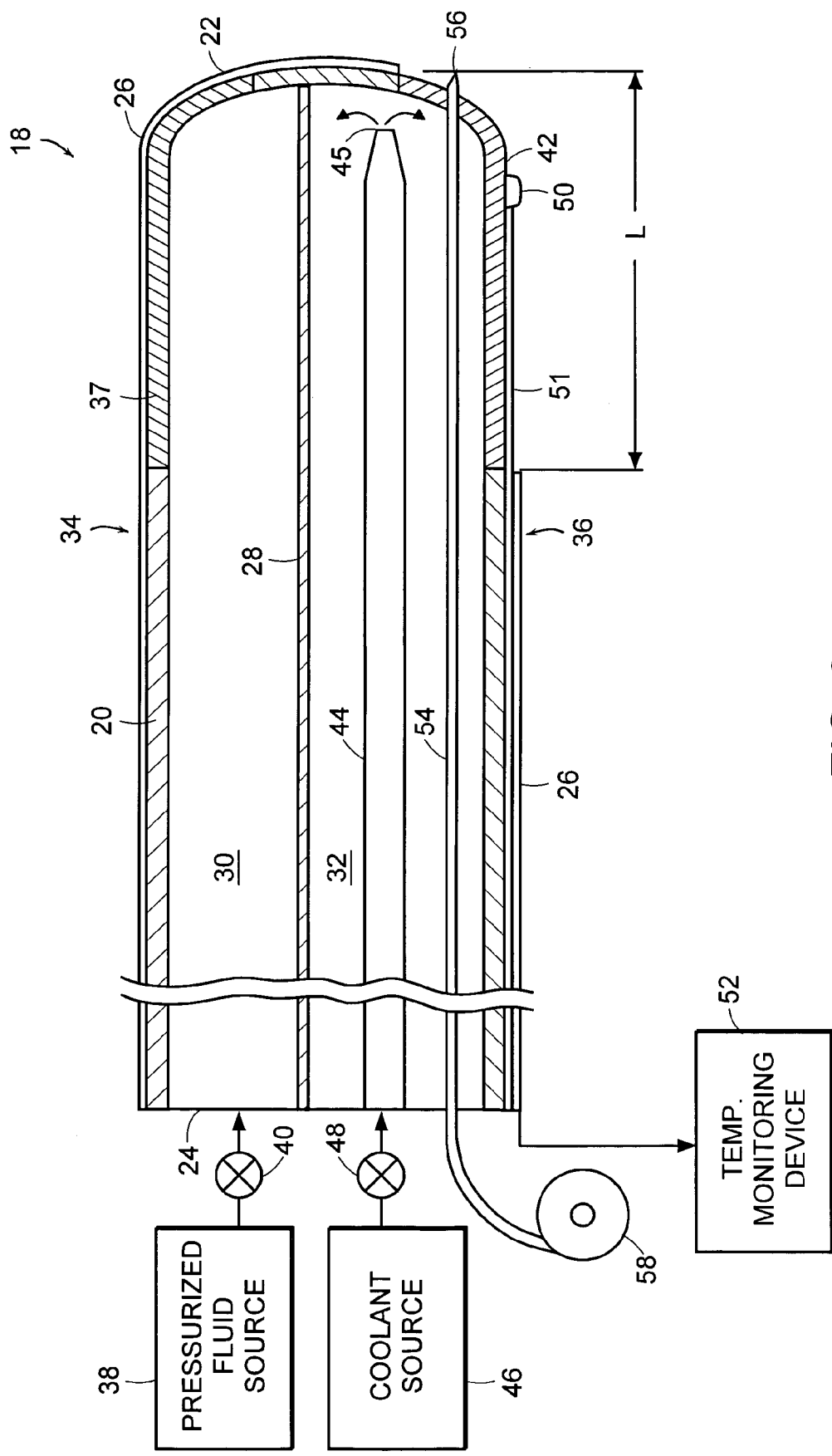
FIG. 3 is an axial cross-sectional view of the cryocatheter of FIG. 2.
Figure 4:
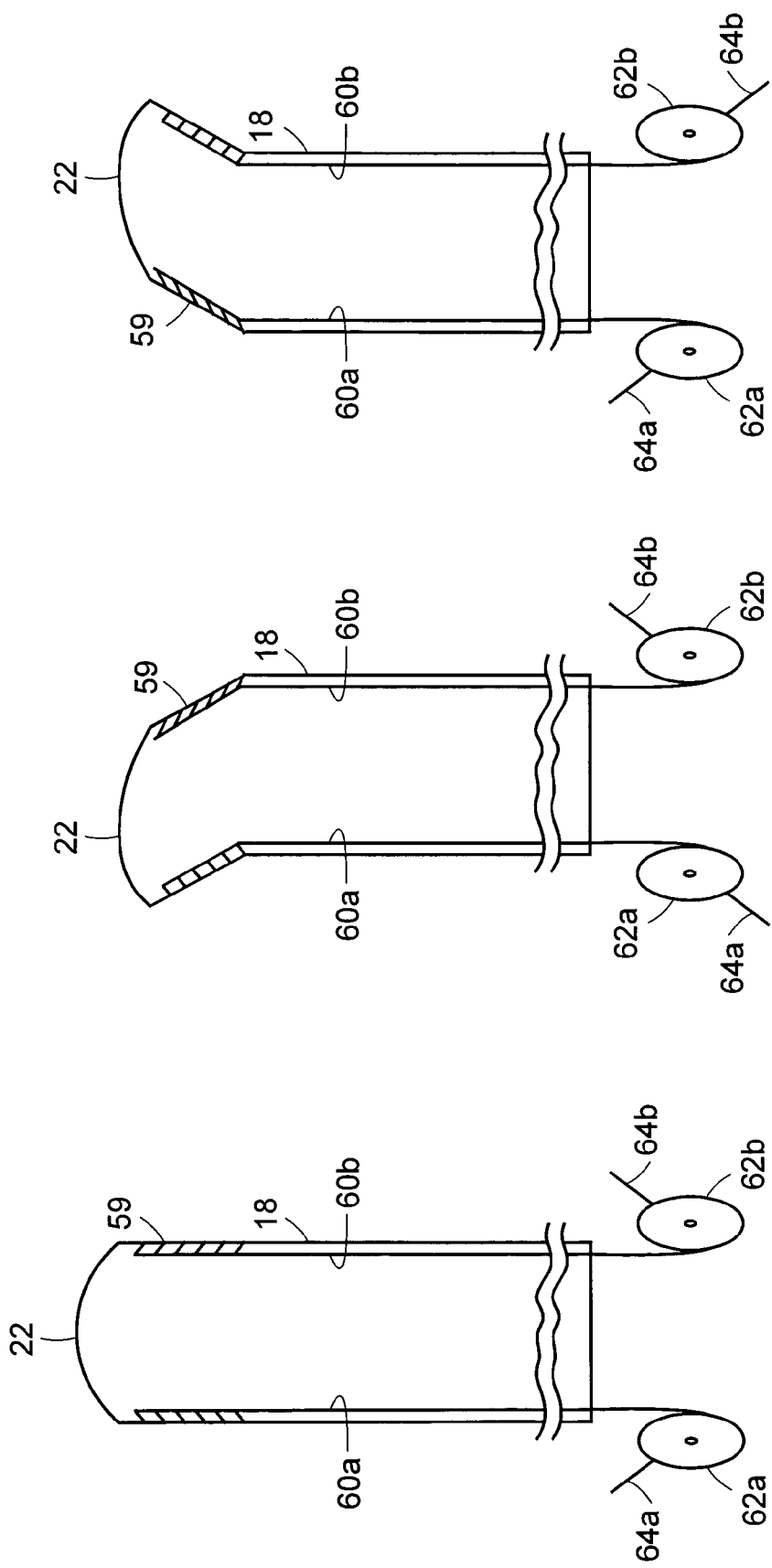
FIGS. 4A-4C are schematic views of the cryocatheter showing a means for angling a distal tip portion of the cryocatheter.

FIGS. 2 and 3 show a cryocatheter 18 for insertion into the sheath 14 after the sheath 14 has been positioned in the patient's body. The cryocatheter 18 has a diameter small enough to fit into the sheath 14 and has a length of about 6-36 inches. The cryocatheter 18 includes a catheter body 20 in the form of a hollow outer tube having a distal end 22 that is insertable through the positioned sheath 14 and a proximate end 24 that remains outside of the body. Although the outer tube 20 is shown as having a circular cross-section, it should be noted that the present invention is not so limited and the cryocatheter 18 can have a variety of configurations. The catheter body or outer tube 20 is made of a non-rigid material and is thermally insulated with a coating 26 of insulating material. A septum 28 is formed inside the outer tube 20 and extends the length thereof to divide the tube interior into first and second chambers 30 and 32. When the cryocatheter 18 is in use, the section thereof encompassing the first chamber 30 will correspond to the dorsal or posterior side of the cryocatheter 18, and the section encompassing the second chamber 32 will correspond to the ventral or anterior side of the cryocatheter 18. The cryocatheter 18 thus has a dorsal side 34 and a ventral side 36. The cryocatheter 18 is preferably made, at least in part, of a material suitable for radiological imaging.

The outer tube 20 has an expandable portion 37 formed at the distal end 22, on the dorsal side 34 so as to be in fluid communication with the first chamber 30. The expandable portion 37 comprises a section of expandable material formed in the outer tube 20. The remainder of the outer tube 20 is made of a material that is not expandable, or at least not as expandable as the material of the expandable portion 37. A pressurized fluid source 38 is connected with the first chamber 30 via a valve 40. The valve 40 can be operated to allow pressurized fluid from the source 38 to flow into the first chamber 30 and inflate the expandable portion 37 so that the distal end 22 is larger in cross-section than the rest of the outer tube 20. The valve 40 can also be operated to allow pressurized fluid to escape from the first chamber 30 so that the expandable portion 37 deflates.

The outer tube 20 includes a tip member 42 formed on the external surface of the ventral side 36, at the distal end 22. The tip member 42 is made of an electrically conducting material and is not thermally insulated. That is, the coating 26 does not cover the tip member 42. A coolant delivery tube 44 is disposed in the second chamber 32, preferably coaxial therewith. One or more expansion openings 45 are formed in the distal end of the coolant delivery tube 44, which is located adjacent to the distal end 22 of the outer tube 20 and the tip member 42. The proximate end of the coolant delivery tube 44 is connected to a source of pressurized coolant fluid (gas or liquid) 46 via another valve 48. The pressurized coolant fluid flows, under control of the valve 48, down the coolant delivery tube 44 and exits through the expansion opening(s) 45 into the second chamber 32. The coolant fluid expands and cools as it is discharged through the expansion opening(s) 45. Thus, the temperature of the non-insulated tip member 42 will be greatly reduced in a controllable manner such that neuronal tissue in contact with or adjacent to the tip member 42 will be cooled or frozen. The spent coolant fluid flows back through the second chamber 32 and exits through the proximate end 24 in a manner known in the art.

It should be noted that the present invention is not limited to a catheter body comprising a single tube separated into two chambers by a septum. Another possible configuration includes a catheter body formed from two catheters joined together lengthwise. One of the catheters would be an expandable catheter corresponding to the dorsal side 34; the other catheter would be a cryocatheter corresponding to the ventral side 36.

The geometry of the tip member 42 will be determined based on the location and nature of the anatomic target site to be treated, which are discussed in more detail below. Generally, the tip member 42 has a substantially semi-cylindrical shape, as shown in FIG. 2. The length, L, of the tip member 42 (FIG. 3) will be dependent on the anatomic target site to be treated. For example, given the arrangement of afferent filaments entering the dorsal horn (i.e., filaments may enter over several centimeters of the cord for a single nerve), the tip member length would be approximately equal to this length if the nerve filaments are the target. If the target were a dorsal ganglion, a shorter, smaller diameter tip member 42 would be desirable. If the entire posterior cord were to be treated, a longer tip member would be used. If generalized cooling of a substantial part or segment of the cord itself is desired (as to induce spinal anesthesia), then the tip member 42 would be configured to accommodate that objective.

A temperature detector 50 is located on the external surface of the tip member 42. The temperature detector 50, which can be any suitable device such as a thermocouple, can be used to provide feedback, via electric wire 51 connected to an external temperature monitoring device 52, of the tip member temperature during a treatment procedure so that the flow of coolant fluid can be controlled accordingly to obtain the desired temperature.

The cryocatheter 18 optionally includes a hollow conduit 54 disposed inside the second chamber 32 of the outer tube 20, adjacent to the coolant delivery tube 44. The hollow conduit 54 has a distal needle tip 56 and is movable longitudinally within the outer tube 20 by a rotatable head 58 located outside of the tube 20 and attached to the proximate end of the hollow conduit 54. The needle tip 56 can be extended beyond the distal end 22 (as shown in FIG. 3) or retracted back into the outer tube 20 by turning the rotatable head 58 in the appropriate direction. The head 58 can be calibrated so as to indicate how much the needle tip 56 is extended. With the needle tip 56 extended, the hollow conduit 54 can be used for local injections of pharmaceuticals. The hollow conduit 54 could be used diagnostically to verify the proper location of the distal end 22. That is, once the distal end 22 was believed to be located at the desired target site, a small dose of an analgesic drug could be injected via the hollow conduit 54. If the patient experienced pain relief in the affected part, this would indicate that the distal end 22 and the tip member 42 are properly located. As an alternative embodiment, it is possible to use a catheter tip configured to deliver pharmaceuticals in gel form.

In addition, the cryocatheter 18 optionally includes a means for changing the angle of a distal tip portion 59 of the cryocatheter 18 relative to the rest of the cryocatheter 18. One possible tip angle changing means is illustrated schematically in FIGS. 4A-4C. In this arrangement, two guide wires 60a and 60b are disposed inside the outer tube 20 on diametrically opposing sides thereof. As seen in FIG. 2, the guide wires 60a and 60b are located adjacent to the opposing sides of the septum 28 so as to provide for lateral adjustment of the tip angle. The distal end of each guide wire 60a and 60b is fixedly attached to the distal tip portion 59 of the outer tube 20. A first rotatable head 62a is located outside of the tube 20 and is attached to the proximal end of the first guide wire 60a, and a second rotatable head 62b is located outside of the tube 20 and is attached to the proximal end of the second guide wire 60b. The first and second rotatable heads 62a and 62b are rotatively mounted to a handle (not shown) and have first and second levers 64a and 64b, respectively, formed thereon. The levers 64a and 64b are positioned such that a user holding the handle can manipulate the levers 64a and 64b independently to turn the corresponding rotatable head 62a and 62b. Turning the first and second heads 62a and 62b in the appropriate direction will pull the corresponding guide wire 60a and 60b relative to the outer tube 20. Because the far end of each guide wire 60a and 60b is fixedly attached to the distal tip portion 59, pulling one of the guide wires 60a and 60b causes the distal tip portion 59 to bend relative to the rest of the outer tube 20. (The catheter structures are all made of a flexible material.) Specifically, pulling the first guide wire 60a causes the distal tip portion 59 to bend to the left as shown in FIG. 4B, while pulling the second guide wire 60b causes the distal tip portion 59 to bend to the right as shown in FIG. 4C. The rotatable heads 62a and 62b are calibrated so that the tip angle can be accurately controlled. Adjusting the tip angle permits the tip member 42 to be positioned adjacent to a wider range of neuroaxis targets.

As mentioned above, the tip member 42 is electrically conducting and can thus function as an electrode for electrodiagnostic purposes. This is accomplished using sensory evoked potentials, which are central nervous system electrical potentials that have traditionally been measured from scalp electrodes after a stimulus is applied to a peripheral nerve or a dermatome. (A dermatome is an area of skin contributing sensory afferent nerve fibers to a spinal nerve(s); there is an anatomic correspondence between a given dermatome and a given dorsal nerve root.) Because evoked potentials as currently measured are remote from the stimulus and are the result of multiple neuronal interactions, they are small in amplitude and difficult to measure above background noise using conventional equipment.

Figure 5:
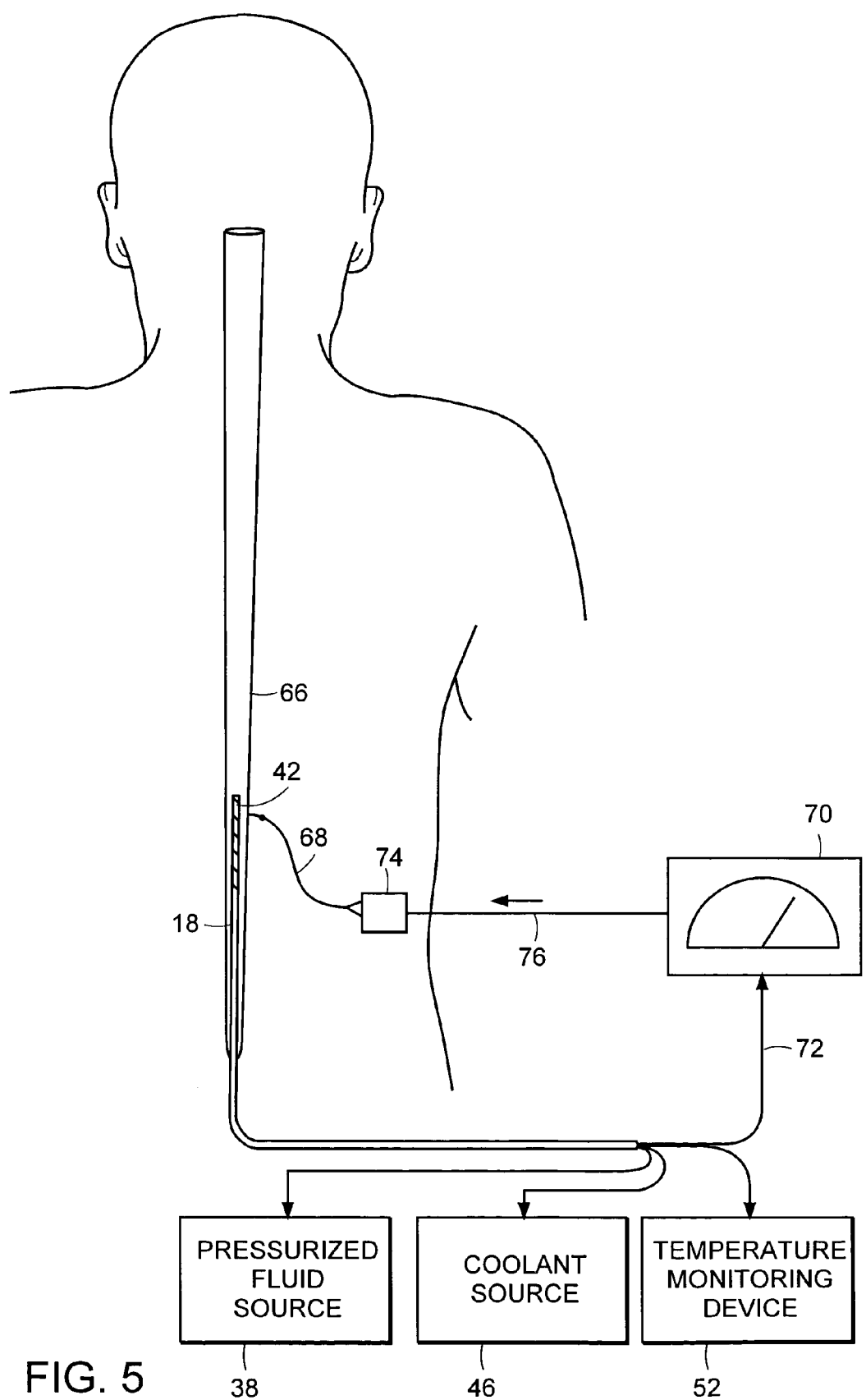
FIG. 5 is a schematic view of a circuit for measuring sensory evoked potentials in a patient.

The electrodiagnostic methods of the present invention are illustrated in FIG. 5, which schematically shows the cryocatheter 18 positioned in a patient's neuroaxis 66. A monitoring/stimulating device 70 is electrically connected to the tip member 42 (functioning as an electrode) via a first electrical lead 72 that passes through the cryocatheter 18. One or more external electrodes 74 are applied to the exterior of the patient's body, on the dermatome that corresponds to the desired neuronal target site in the neuroaxis. The external electrode(s) 74 is electrically connected to the monitoring/stimulating device 70 via a second electrical lead 76. The monitoring/stimulating device 70 is capable of generating an electrical stimulus for stimulating nerve endings of a dermatome. The monitoring/stimulating device 70 is also capable of receiving signals from the tip member 42 and measuring and displaying evoked potentials in response to such signals. Many devices for measuring and displaying evoked potentials are commercially available. The monitoring/stimulating device 70 can be any device suitable for such use, including commercially available devices, except that the device 70 will be used with the tip member 42 as the detecting electrode instead of a conventional scalp electrode.

When the tip member 42 is believed to be located at the desired target site in the neuroaxis, a measured electrical stimulus is applied to the corresponding dermatome via the external electrode(s) 74. This electrical stimulus will be conducted centrally by the corresponding sensory (afferent) nerve 68, including the target neuronal tissue, to the spinal cord. If the tip member 42 is in contact with the appropriate target neuronal tissue, an electrical circuit will be completed. That is, the electrical stimulus will be conducted from the monitoring/stimulating device 70 to the external electrode(s) 74 via the second electrical lead 76, from the external electrode(s) 74 to the tip member 42 via the sensory (afferent) nerve 68, and from the tip member 42 to the monitoring/stimulating device 70 via the first electrical lead 72. The monitoring/stimulating device 70 thus provides detection of the dermatomal sensory evoked potential when the tip member 42 is properly located. The design of the cryocatheter 18, which provides for direct contact of the tip member 42 with the target neuronal tissue (as opposed to an electrode on the patient's scalp), greatly enhances the magnitude, sensitivity and specificity of the dermatomal sensory evoked potential.

When the device 70 detects a sensory evoked potential, this serves as an indication that the tip member 42 is properly positioned. At this point, the cooling/freezing treatment of the target site can be carried out. As the target neuronal tissue is cooled, nerve conduction will be interrupted (before freezing) and thereby eliminate or reduce pain. Moreover, nerve conduction interruption will also result in cessation of the sensory evoked potential. Thus, induced functional impairment of the target neuronal tissue will be confirmed when the device 70 ceases to measure a sensory evoked potential. This further verifies that the tip member 42 has been properly positioned and means that protracted cooling or freezing can be carried out to complete the procedure.

As mentioned above, the neuro-cryocatheter system provides cryoanalgesia by cooling or freezing of neuroaxis structure targets. Cooling mixed nerves produces a nerve conduction block wherein motor function is affected before sensory function. Selection of sensory, dorsal nerve structures as targets for cooling/freezing will render this irrelevant. The motor function is in the ventral nerve root, separated from the dorsal root by the denticulate ligament. Large myelinated sensory (afferent) fibers are affected and cease conduction before unmyelinated fibers. Small diameter myelinated fibers appear to be the most sensitive to cold. The most common neuronal tissue associated with pain is a small diameter unmyelinated fiber in the dorsal root.

When cooling neuronal tissue, the nerve conduction block is complete above 0 degrees centigrade, but prolonged conduction disturbances occur only by achieving temperatures of −5 to −20 degrees centigrade. At temperatures between −5 and −20 degrees centigrade neuropraxis may occur without neuronal destruction. Freezing generally occurs at temperatures below −20 degrees centigrade. Once freezing has occurred, no benefit is obtained by achieving by lower temperatures. There is little inflammatory response to freezing and if tissue structures (for example, the endoneurium) are not disrupted, nerve regeneration is possible. Recovery from freezing is accomplished in cases where axon destruction is followed by axonal regeneration. This process of regeneration has been studied and reported in medical literature.

In operation, cryocatheter 18 is introduced into the subarachnoid space of the spinal canal (dorsal aspect) by percutaneous spinal canal puncture. Specifically, after skin preparation, the introducer 10 is inserted into the subarachnoid space at the desired location, and the stylet 12 is removed, leaving the sheath 14 in place to function as a cannula. The structure of the meninges is such that the subarachnoid space can be entered posteriorly, by percutaneous puncture between the spinous processes. The distal end 22 of the cryocatheter 18 is inserted through the sheath 14 and into the subarachnoid space on the dorsal side of the spinal cord. The cryocatheter 18 is oriented such that the expandable portion 37 faces the dorsal dura mater and the tip member 42 faces the dorsal side of the spinal cord.

The distal end 22, and hence the tip member 42, are advanced to the target neuronal tissue. Proper positioning of the distal end 22 can be accomplished with imaging guidance. For instance, providing the cryocatheter 18 with a radioopaqueness allows the distal end 22 to be placed adjacent to the target neuronal tissue with the aid of radiological imaging. The cryocatheter 18 could also be made of non-magnetic (non-polarizable) material for use in an open MRI device. The external electrode(s) 74 is placed on the patient's body, on the dermatome that corresponds to the target neuronal tissue, and the device 70 is turned on such that the electrodiagnostic function of the cryocatheter 18 is operating.

Figure 6:
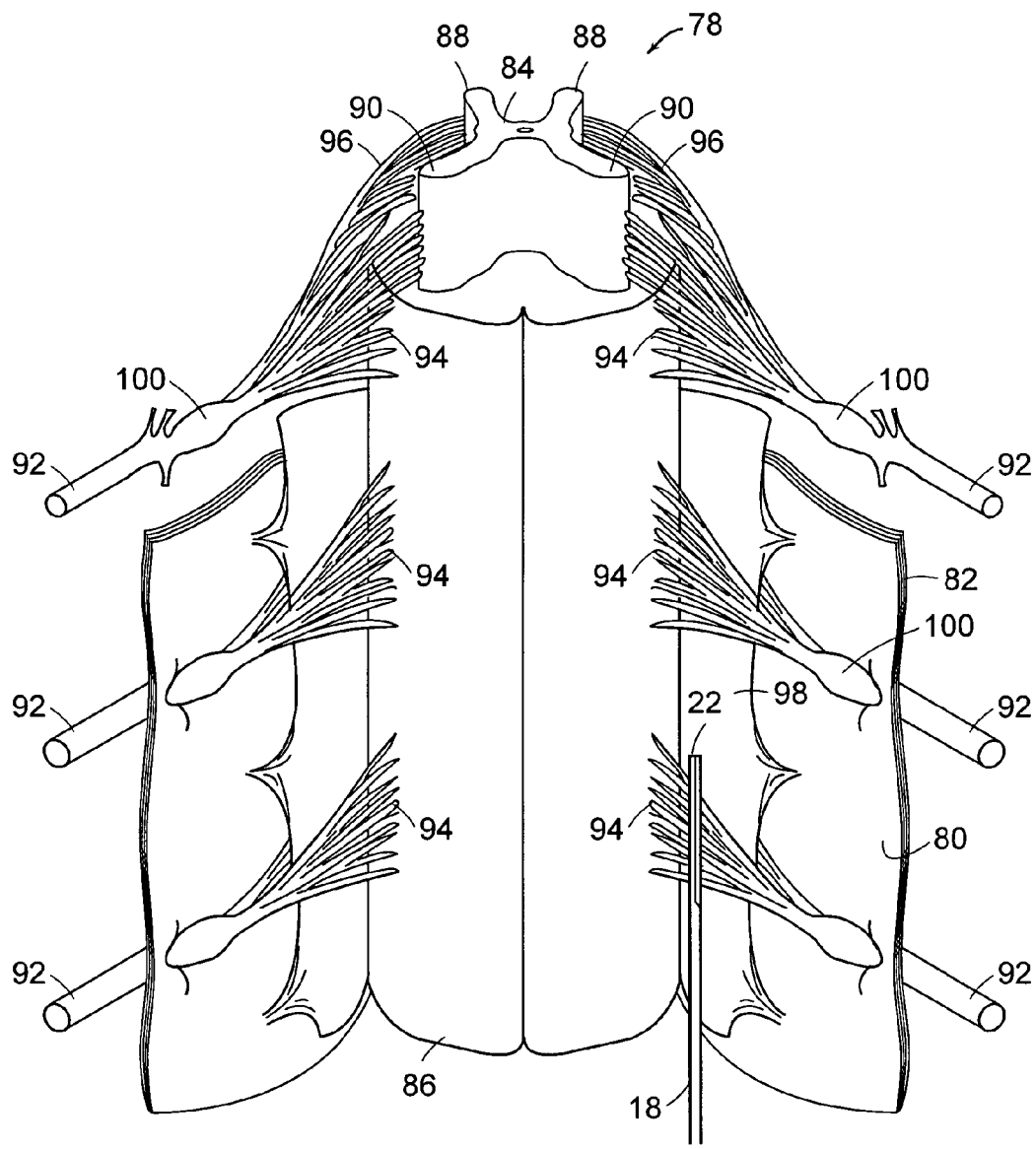
FIG. 6 is a dorsal view, in partial cutaway, of a portion of a spinal cord.

There are many possible neuroaxis structure targets that could be selected for cooling or freezing with cryocatheter 18. Referring to FIG. 6, which is a dorsal view of a portion of a spinal cord 78 with the arachnoid mater 80 and the dura mater 82 shown pulled back, the basic structure of the neuroaxis and its possible targets will be described. The spinal cord 78 is comprised of the interior gray matter 84 and the white matter 86, which encompasses the gray matter 84. The gray matter 84 includes two ventral horns 88 and two dorsal horns 90. The arachnoid mater 80 completely surrounds the spinal cord 78, and the dura mater 82 surrounds the arachnoid mater 80. The subarachnoid space, several millimeters in depth and filled with spinal fluid, lies between the spinal cord 78 and the arachnoid mater 80. There are 30 paired spinal nerves 92 emanating from the spinal cord (8 cervical, 12 thoracic, 5 lumbar, 5 sacral), three of which are shown in FIG. 6. Each spinal nerve 92 is divided into dorsal root filaments 94 and ventral root filaments 96 within the subarachnoid space. The dorsal root filaments 94, which are composed of sensory nerve fibers, enter the dorsal horn 90 of the spinal cord 78. The ventral root filaments 96, which are composed of motor nerve elements, emanate from the ventral horn 88. The anatomic separation is accentuated by the denticulate ligament 98, which lies between the dorsal root filaments 94 and the ventral root filaments 96. The nerve root filaments are made up of nerve axons. The dorsal root ganglia 100, which lie laterally of the dorsal root filaments 94 in the subarachnoid space, contain the neuronal bodies of most of the afferent nerve axons. With the exception of the head, the dorsal root filaments 94 of the paired spinal nerves 92 supply the major sensory input of the body.

Accordingly, the dorsal root filaments 94 are a primary target for cooling or freezing. Because these are sensory nerve structures, interrupting conduction by cooling or freezing will reduce or eliminate pain that would otherwise be transmitted by the nerve structures. The ventral root elements 96 (which are separated from the dorsal root elements by the denticulate ligament) are concerned with motor function and generally are not targets for the relief of pain. Other possible targets include the dorsal root ganglia 100, which contain the neuronal cell bodies of the dorsal root elements, and the dorsal horn 90 (particularly Rexed levels 1-4, or even Rexed levels 1-5). Lissauer's tract, which is adjacent to the dorsal horn 90, is also a potential target for cooling or freezing.

Visceral afferent nerve fibers conducting pain signals also enter the spinal cord via the dorsal roots. By rendering the dorsal root neuronal elements or the dorsal horn non-functional (non-conductive) along the cord at various levels both visceral and peripheral nerve sensory afferents can be controlled. It should therefore be possible to alleviate pain in viscera by cooling or freezing the appropriate spinal targets. For example, pancreatic pain could be alleviated this way.

As mentioned above, the distal end 22 of the cryocatheter 18 is inserted into the subarachnoid space and advanced until the tip member 42 is adjacent to the target neuronal tissue. For example, the distal end 22 is schematically shown as being adjacent to a set of dorsal root filaments 94 in FIG. 6. With the tip member 42 believed to be properly positioned adjacent to the target tissue, the dorsal expandable portion 37 of the cryocatheter 18 is inflated with pressurized fluid from the source 38, as controlled by the valve 40, until it expands into contact with the arachnoid mater 80 and the adjacent dura mater 82 and presses the tip member 42 on the ventral surface of the cryocatheter 18 into contact with the dorsal neuronal target. Thus, inflation of the expandable portion 37 holds the distal end 22 in position relative to the target neuronal tissue. As discussed above, reception of dermatomal sensory evoked potentials by the device 70 indicates that the tip member 42 is properly positioned.

Once the tip member 42 is fixed in the proper position, the valve 48 is opened to admit a flow of coolant fluid to the coolant delivery tube 44. The coolant fluid exits the tube 44 via the opening(s) 45, expands, and thereby cools the tip member 42. The temperature of the tip member 42 is monitored by the temperature detector 50. By monitoring the tip member temperature, the operator will be able to control the flow of coolant fluid so as to gradually cool the tip member 42, and hence the neuronal target tissue. Functional impairment of the target neuronal tissue induced by cooling or freezing will be confirmed by cessation of the dermatomal evoked sensory potential measured by the device 70.

Depending on the goals of the procedure, the neuronal tissue will be cooled or frozen. If cooled, the procedure may be carried out for extended periods of time. If neuronal tissue is frozen, continued application of the freezing process beyond that necessary to achieve at least −20 degrees centigrade is unnecessary.

If the cryocatheter 18 is being used for diagnostic purposes only (i.e., being used to determine the functional status of neuronal tissue), the procedure is the same as that described above except that the cooling/freezing steps are omitted and the diagnostic information would be obtained by measuring dermatomal sensory evoked potentials off the neuronal tissue while stimulating the appropriate dermatome. For example, the use of this function could maintain spinal cord function during neuro-surgery.

The affect of cooling or freezing of neuroaxis tissue will be impacted by the particular anatomic site chosen (the target neuronal tissue), the rate of cooling or freezing, the temperature achieved, the duration of cooling in some circumstances, and thawing/freezing cycles, if employed. (Thawing/freezing cycles refers to small ice crystals thawing and the water being subsequently refrozen by larger ice crystals.) Freezing results in the withdrawing of water from biologic systems and the deposition of water in ice crystals. The development of ice crystals depends upon a) crystal nucleation rate and b) the ice crystal growth rate. Both of these factors are dependent on temperature and the rate of cooling. These factors are also tissue type specific and may not be linear with fall in temperature. The location of the ice crystals (i.e., intracellular versus extracellular) is dependent on the rate of cooling, with rapid freezing promoting the formation of intracellular ice crystals and increasing the risk of ultimate cell death. The size of the crystals for a given amount of water (in tissue) is a function of the number of crystals initiated by the process. The rate of temperature fall may well be a dominant variable. This in turn will be a function of efficiency by which a system removes heat. Anatomic considerations, such as blood vessel supply (blood flow) and cerebrospinal flow rates, may well impact the cooling rate. Recrystallization (i.e., the growth of large crystals at the expense of smaller ones) will influence the final nature and the extent of tissue damage and may occur during thawing. Thawing/freezing cycles, if employed, will impact the final lesion.

When the rate of cooling is slow, ice crystal nucleation occurs in the extracellular space drawing water out of the cell. The result is a formation of a few large, generally extracellular, crystals. The further result is such as to leave the cell membrane largely intact; membrane rupture is uncommon. This is useful when freezing nerve axons, leaving the endoneurium intact which allows for axonal regeneration. Extracellular ice crystal formation is unlikely to cause cell death even if the cell body is cooled or frozen. Freezing of vascular tissue that results in ischemia of the end-organ tissue may also be a factor in the destruction of the cell within the ice ball. However, the vascular supply of the spinal cord appears diffuse with multiple collaterals such that ischemia may not be a problem.

The geometry of the tip member 42 is a factor in lesion production since the tissue immediately adjacent to the tip member 42 will freeze more quickly and thoroughly. Moreover, the size of the ice ball, a field of cooling gradients, is correlated to the tip geometry. This could result in intracellular ice near the tip member 42 and extracellular ice away from the tip member 42. In any event, it is anticipated that there will be a freezing gradient related to the tip member 42 and its configuration.

Neuronal cell death (as opposed to axonal disruption) is likely to occur when a critical temperature achieved. This is believed to be −4 degrees centigrade or below and certainly is reached at −20 degrees centigrade. This temperature may be somewhat tissue dependent (for example, red blood cell versus neuronal tissue). There are reports of neuronal recovery for temperatures as low as −15 degrees centigrade. However, there appears to be a consensus that cells do not survive at temperatures lower than −20 degrees centigrade. Neuronal generation and conduction of nerve electropotentials ceases during cooling, but before nerve tissue is frozen. In addition, the electrical impedance of the tip member 42 goes up as ice is formed on it. Controlled cooling of the tip member 42 and the target tissue can avoid this and allow sensory evoked potential measurement.

An up to two hour exposure of neuronal tissue to cold temperature (e.g., between +5 and −5 degrees centigrade) will cool but not freeze the tissue and produce transient interruption of nerve conduction lasting hours or even days. When a mixed nerve is cooled, motor function is affected before sensory function. However, as previously noted, cooling the dorsal root or horn and the posterior cord itself should impact sensory function alone and not motor function. When neuronal cell bodies are frozen to −20 degrees centigrade or below, the duration of freezing becomes irrelevant because of the likelihood of cell death occurring.

If axons or nerve bodies are cooled, the return of function will return relatively quickly (i.e., over the course of many hours to several days). If axons are frozen, return of function will take many days or weeks as degeneration/regeneration of axons occur (axonal tissue regenerates at approximately 1-3 millimeters per day). If nerve bodies are frozen, neuronal function will generally not return. Accordingly, the target tissue should be selected carefully.

An alternative embodiment to the neuro-cryocatheter system described above would be to provide the cryogenic, electrodiagnostic, and pharmaceutical delivery functions with two or more catheters rather than a single catheter. Such an alternative system would include an introducer the same as or similar to the introducer 10 of FIG. 1 and a plurality of catheters. For instance, there could be a cryocatheter having cryogenic capabilities for cooling or freezing of neuroaxis structure targets and a separate catheter for delivering pharmaceuticals. There could also be another catheter having an electrode like the tip member 42 but no cryogenic capability. Such a catheter would be used for diagnostic purposes only (i.e., for determining the functional status of neuronal tissue).

While specific embodiments of the present invention have been described, it will be apparent to those skilled in the art that various modifications thereto can be made without departing from the spirit and scope of the invention as defined in the appended claims.

What is claimed is:

1. A catheter for cooling or freezing neuroaxis structure targets, said catheter comprising:

a. a catheter body having a proximal end and a distal end and a dorsal side and a ventral side wherein said catheter body is a tube having an interior and a septum formed in said tube interior, said septum dividing said tube interior into a dorsal chamber on said dorsal side and a ventral chamber on said ventral side and wherein neither chamber is disposed within the other chamber;

b. an expandable portion located at the distal end of the dorsal chamber that can be transitioned from a first state to a second state in order to secure the distal end of said catheter body in position adjacent to a neuroaxis structure target;

c. a delivery tube disposed within said ventral chamber for internally delivering a coolant fluid to the ventral chamber of said ventral side of said distal end of said catheter body and wherein said septum prevents said coolant from entering said dorsal side and returns said coolant fluid to said proximal end of said catheter body without said coolant fluid coming into direct contact with said neuroaxis structure targets; and d. wherein said cooling or freezing effect is adapted to be delivered to neuroaxis structure targets located on the ventral side of said catheter and not to tissues located on the dorsal side of said catheter and wherein the angle of said distal end of said catheter can be changed relative to the body of the catheter.

2. The catheter of claim 1, wherein said catheter body is sized and dimensioned for insertion into the subarachoid space of a patient.

3. The catheter of claim 1, wherein said expandable portion is changed from the first state to the second state by delivery of pressurized fluid to said expandable portion.

4. The catheter of claim 3, wherein said expandable portion is expanded by a pressurized fluid source connected to said dorsal chamber for inflating said expandable portion.

5. The catheter of claim 1, wherein a source of coolant fluid is connected to said delivery tube.

6. The catheter of claim 5, wherein said delivery tube has at least one expansion opening located near said distal end of said catheter body.

7. The catheter of claim 1, wherein at least a portion of said catheter is made of a material suitable for imaging.

8. The catheter of claim 7, wherein at least a portion of said catheter is made of a material suitable for radiological imaging.

9. The catheter of claim 7, wherein at least a portion of said catheter is made of a material suitable for MRI imaging.

10. The catheter of claim 1, further comprising a non-separable temperature detector disposed proximate the external surface of said catheter body, at said distal end thereof, wherein said temperature detector measures the temperature of the neuroaxis structure targets.

11. The catheter of claim 1, further comprising:
a. an electrically conductive tip member formed on an external surface of said catheter body, at said ventral side of said distal end thereof; and
b. wherein the electrically conductive tip member is electrically connected to an external device.

12. The catheter of claim 1, wherein said angle of said distal end of said catheter is changed relative to the body of the catheter by a control mechanism mechanically connected to a control device external to the patient.

13. The catheter of claim 1, further comprising a conduit disposed in said catheter body, said conduit having a tip and being movable longitudinally within said catheter body such that said tip can be extended out of and retracted into said catheter body.

14. The catheter of claim 1, further comprising a non-separable temperature detector disposed proximate the external surface of said catheter body, at said distal end thereof, wherein said temperature detector measures the temperature of the neuroaxis structure target-catheter interface.

15. A catheter system for cooling or freezing neuroaxis structure targets, said catheter system comprising:

a. a catheter body having a proximal end and a distal end and a dorsal side and a ventral side, said catheter body being sized and dimensioned for insertion into the subarachnoid space of a patient and wherein said catheter body is a tube having an interior and a septum formed in said tube interior, said septum dividing said tube interior into a dorsal chamber on said dorsal side and a ventral chamber on said ventral side wherein neither chamber is deposed within the other chamber;

b. a tip member formed on said ventral side of said catheter body, at said distal end thereof;

c. an expandable portion formed at the distal end of said dorsal side of said catheter body for holding the distal end of said catheter body in position adjacent to a neuroaxis structure target;

d. a delivery tube disposed within said ventral chamber suitable for carrying coolant to said tip member for moving a cooling fluid from said proximal end of said catheter to said distal end of said catheter through said delivery tube and returns said coolant fluid to said proximal end of said catheter without said coolant fluid coming into direct contact with said neuroaxis structure targets; and e. wherein said cooling or freezing effect is adapted to be delivered to neuroaxis structure targets located on the ventral side of said catheter and not to tissues located on the dorsal side of said catheter and wherein the angle of said distal end of said catheter can be changed relative to the body of the catheter.

16. The catheter system of claim 15, wherein said expandable portion is expanded by delivery of pressurized fluid to said expandable portion.

17. The catheter system of claim 16, wherein said expandable portion is expanded by a pressurized fluid source connected to said dorsal chamber for inflating said expandable portion.

18. The catheter system of claim 15, wherein a source of coolant fluid is connected to said delivery tube, said delivery tube having at least one expansion opening located near said tip member.

19. The catheter of claim 18, further comprising an electromechanical system for controlling delivery of coolant fluid to said delivery tube in response to a signal from a non-separable temperature sensor proximate to said tip member.

20. The catheter system of claim 15, wherein at least a portion of said catheter body is made of a material suitable for radiological imaging.

21. The catheter system of claim 20, wherein at least a portion of said catheter body is made of a material suitable for radiological imaging.

22. The catheter system of claim 20, wherein at least a portion of said catheter body is made of a material suitable for MRI imaging.

23. The catheter system of claim 15, further comprising a non-separable temperature detector disposed proximate to said tip member, wherein said temperature detector measures the temperature of the tissue targets.

24. The catheter system of claim 15, wherein said tip member is electrically conductive, said catheter system further comprising:
a. an external electrode for application to a patient's body; and
b. a device electrically connected to said tip member and to said external electrode, said device being capable of delivering an electrical stimulus to said external electrode and measuring sensory evoked potentials in response to input from said tip member.

25. The catheter system of claim 15, wherein said the angle of said distal end of said catheter is changed relative to the body of the catheter by a control mechanism mechanically connected to a control device external to the patient.

26. The catheter system of claim 15, further comprising a conduit disposed in said catheter body, said conduit having a needle tip and being movable longitudinally within said catheter body such that said needle tip can be extended out of and retracted into said catheter body.

* * * * *